United States Patent [19]

Gausmann et al.

[11] 4,330,206

[45] May 18, 1982

[54] CUVETTE FOR USE IN OPTICAL MEASUREMENTS

[75] Inventors: Hans Gausmann; Walter Geis, both of Aalen, Fed. Rep. of Germany

[73] Assignee: Carl Zeiss-Stiftung, Oberkochen, Fed. Rep. of Germany

[21] Appl. No.: 117,792

[22] Filed: Feb. 1, 1980

[30] Foreign Application Priority Data

Feb. 9, 1979 [DE] Fed. Rep. of Germany ....... 2904909

[51] Int. Cl.³ .............................................. G01N 1/10
[52] U.S. Cl. ................................................... 356/246
[58] Field of Search ................ 356/246, 410, 411, 446

[56] References Cited

U.S. PATENT DOCUMENTS 4,017,190 4/1977 Fischel ........................... 356/411 X

FOREIGN PATENT DOCUMENTS 2221044 9/1974 France ................................. 356/246
247612 12/1969 U.S.S.R. .............................. 356/246

Primary Examiner—John K. Corbin
Assistant Examiner—Matthew W. Koren
Attorney, Agent, or Firm—Hopgood, Calimafde, Kalil, Blaustein & Judlowe

[57] ABSTRACT

The invention contemplates a cuvette or cell construction which is especially adapted to enable photometer or the like measurement of sample fluid admitted to the measurement chamber of the cell. The construction is applicable to fluid analysis under either the condition of a continuous-flow of specimen fluid, or under the condition that a single small sample has been vacuum-induced into the measurement chamber. The construction is inherently simple, is inherently self-clearing of air or gas bubbles in liquid samples, and provides inherently efficient cleansing of the measurement chamber when examined sample is withdrawn.

3 Claims, 2 Drawing Figures

CUVETTE FOR USE IN OPTICAL MEASUREMENTS

BACKGROUND OF THE INVENTION

This invention relates to a cuvette or cell for optical measurements on liquid samples for use as a flow-through or suction cell.

Such cells are used, for instance, in automatic analysis machines in order to receive different solutions one after the other by controlled suction and thus bring them into the optical path of a photometer.

In devices of the character indicated, the measurement channel is usually cylindrical and of relatively small volume, to permit analysis measurement on a small sample quantity, the flat ends of the cylinder being necessary for passage of external radiation through the sample in the measurement channel. But such cylindrical shape does not assure a bubble-free filling, nor does it avoid contamination of one sample by the preceding sample, when different solutions are measured in succession.

Cells of this type are known in which a bubble-free filling is assured by additional chambers connected in front of, behind or parallel to the measurement channel. However, these surface-increasing measures in their turn favor contamination and increase the minimum amount of substances for the measurement, since these at least partially filled additional chambers are not traversed by the radiation. Furthermore, the large number of hollow spaces required for the additional chambers increases the cost of production of such cells.

BRIEF STATEMENT OF THE INVENTION

The object of the present invention is to create a cell of the aforementioned type which is simple to manufacture and permits a bubble-free, low-contamination filling of the measurement channel and which permits use of the smallest possible quantities of the substances to be measured.

This object is achieved in accordance with the invention (a) by providing a measurement channel having an inlet at one end and an outlet at the other end, and wherein the upper wall surface slopes upwardly in the direction of the outlet end of the measurement channel, and (b) by providing two outlet channels at the outlet end, one of which outlet channels communicates with the measurement channel at the highest elevational point of the latter.

By this development, the result is obtained that bubbles of gas in the liquid to be measured move towards the upper end of the exhaust side of the measurement channel and are immediately drawn off there by means of the said one outlet channel, thereby enabling a bubble-free flow of liquid to impinge on the window at the exhaust end. In this way, the advantage is obtained that the liquid to be measured is free of bubbles in the measurement channel proper and the window of the exhaust side is kept free of contamination.

In order to keep also the window of the inlet side free of contamination, it is advantageous if the fluid flowing into the measurement channel strikes said window obliquely. In order to minimize its surface area, the measurement channel has the shape of a hollow cylinder or a cone on which the inlet and outlet openings are arranged at the ends of its generatrix, lying preferably in the same plane.

DETAILED DESCRIPTION

Figure 1:
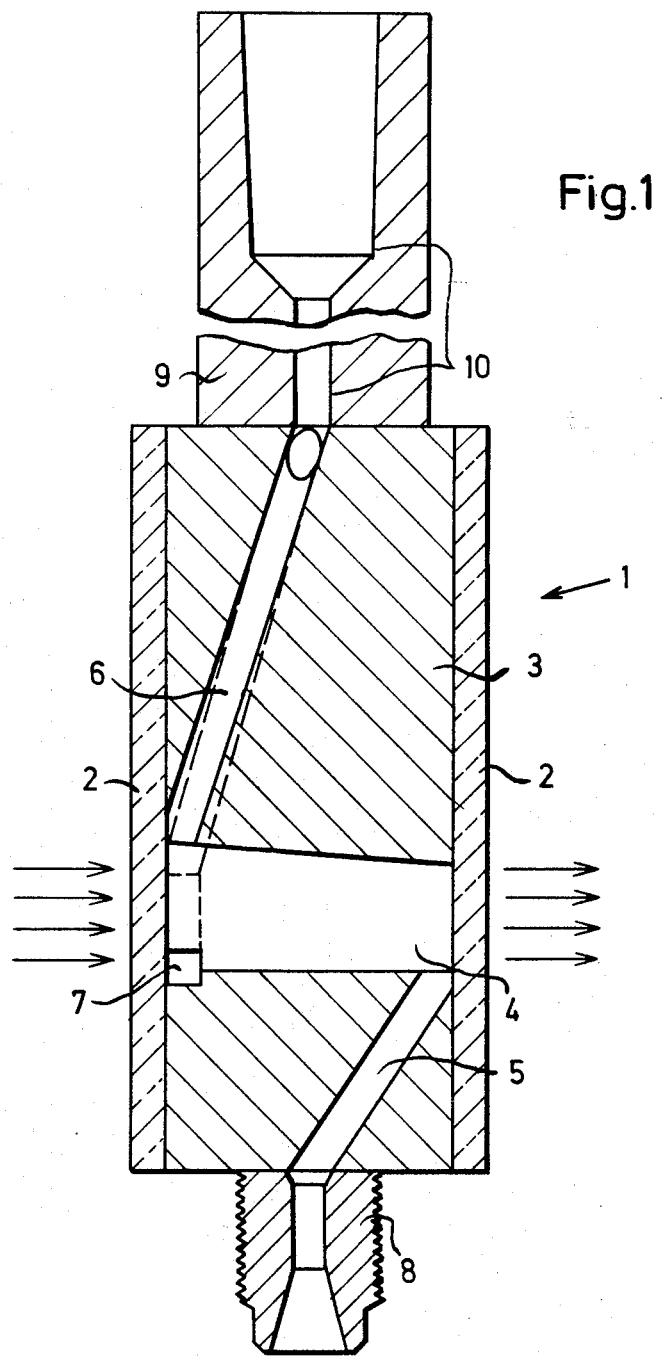
Figure 2:
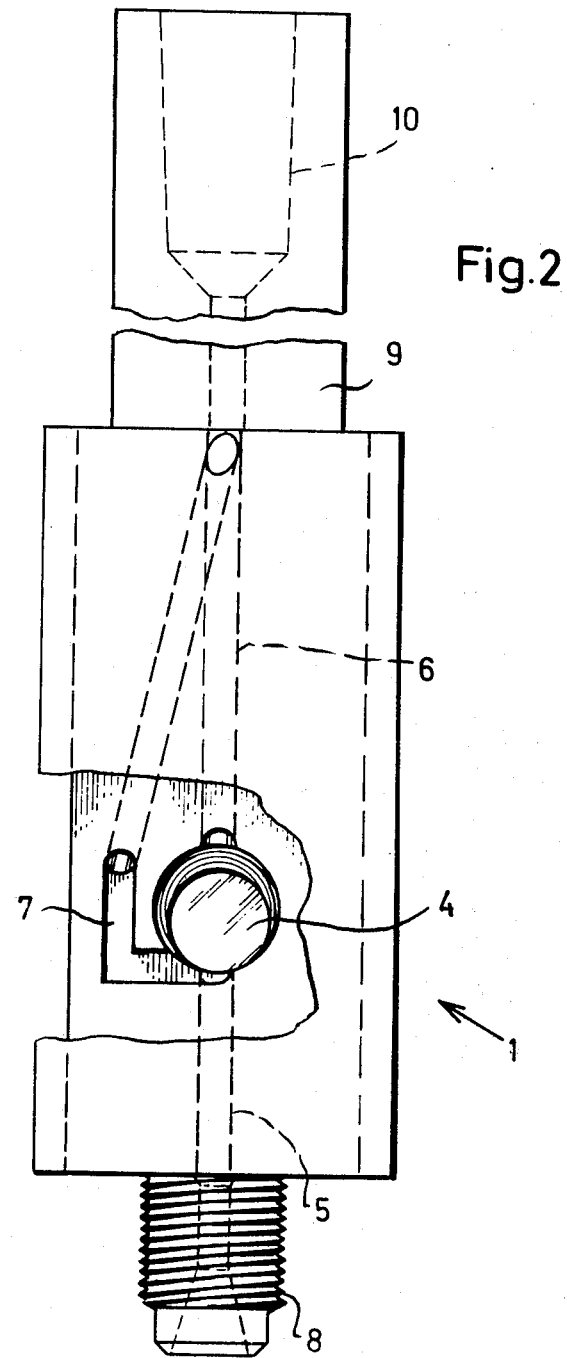

An illustrative embodiment of the invention will be described in conjunction with the accompanying drawings, in which:

FIG. 1 is a longitudinal section through an illustrative cuvette or cell of the invention; and FIG. 2 is a side view of the same cell, partly broken-away to reveal internal construction.

The cuvette or cell 1 shown in FIGS. 1 and 2 consists of a central body part 3 which contains a measurement channel 4 and an inlet channel 5, as well as two outlet channels 6, 7; and two plane-parallel plates 2 on opposite sides of body part 3 close off the measurement channel at its ends and serve the function of radiation windows. A connector piece 8 is attached to the end of the cell which is at the bottom (when in operating condition), and connector piece 8 is the means by which the inlet channel 5 can be connected to various feed hoses.

The upper end of the cell is provided with a similar connector piece 9, and the two outlet channels 6 and 7 discharge into the borehole 10 of the connector piece 9.

The cell is preferably so operated that, for example, a pump produces a vacuum in the measurement channel 4 via the borehole 10, as a result of which the liquids to be examined are drawn into the measurement channel 4 via feed hoses connected thereto via the inlet channel 5. As soon as the measurement channel 4 is filled and any gas bubbles which might be present have escaped along the upper wall of the measurement channel 4 which ascends towards the outlet side, the content of the measurement channel is irradiated.

If sufficient quantities of the liquids to be examined are present, then after the completion of the first measurement, traces of the first sample which would disturb the second measurement are removed by flushing with the new sample. The course of the flow is so favorable, due to the presence of the two outlet openings which discharge into the outlet channels 6 and 7, that freedom of the measurement channel from contamination is rapidly obtained. The oblique course of the inlet channel 5 towards the radiation window also has a favorable effect in this connection.

When making measurements of small amounts of samples, each sample is drawn off after a measurement, so that air rather than a new sample is then drawn through the channels of the cell. The two suction channels and the special shape of their arrangement assure that the measurement channel will be rapidly and completely emptied. Contamination-free operation with small quantities of samples is thus made possible.

With a cell in accordance with the present invention, more favorable contamination values are obtained in both types of operation (flow-through and suction) than with the devices known at the present time. As shown by the embodiment illustrated in FIGS. 1 and 2, its construction can at the same time be kept extremely simple. It is merely necessary to provide a few channels, which may be straight; and the measurement channel 4 may widen conically in the outlet direction, with the upper limit of the conical wall sloping upwardly in the direction of the outlet end of the measurement channel.

Of course, such a cell is not only suitable for measurements which employ radiation in the visible range, since infrared or ultraviolet radiation can, for instance, also be used, provided that the radiation windows 2 are of suitable material.

What is claimed is:

1. In a cuvette cell for optical measurements on liquid samples for use as a flow-through or suction cell wherein a measurement channel has windows for the directional passage of radiation and separate openings for the filling and emptying thereof, said openings being adjacent to said windows, the improvement in which, with respect to the operational orientation of the cell,
   (a) the measurement channel extends approximately horizontally and widens conically in the liquid-flow direction,
   (b) said windows are flat and perpendicular to the direction of said radiation, and
   (c) the opening for emptying said measurement channel comprises two outlet passage means, one of said passage means communicating with the lowest point and the other communicating with the highest point of the outlet end of said channel.

2. In a cuvette cell for optical measurements on liquid samples for use as a flow-through or suction cell wherein a measurement channel has windows for the directional passage of radiation and separate openings for the filling and emptying thereof, said openings being adjacent to said windows, the improvement in which, with respect to the operational orientation of the cell,
   (a) the measurement channel extends approximately horizontally and has an upper wall surface which slopes upwardly in the liquid-flow direction,
   (b) said windows are flat and perpendicular to the direction of said radiation, and
   (c) the opening for emptying said measurement channel comprises two outlet passage means, one of said passage means communicating with the lowest point and the other communicating with the highest point of the outlet end of said channel.

3. A cuvette cell according to claim 1 or claim 2, wherein both outlet passage means discharge within the cell into a common outlet.

* * * * *